US008427817B2

(12) United States Patent
Lewis et al.

(10) Patent No.: US 8,427,817 B2
(45) Date of Patent: Apr. 23, 2013

(54) HANDHELD DIABETES MANAGER WITH TOUCH SCREEN DISPLAY

(75) Inventors: Joseph B. Lewis, Indianapolis, IN (US); Derek C. Lotarski, Noblesville, IN (US); Michael F. DeRossi, Lindenhurst, IL (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 270 days.

(21) Appl. No.: 12/905,511

(22) Filed: Oct. 15, 2010

(65) Prior Publication Data
US 2012/0092812 A1 Apr. 19, 2012

(51) Int. Cl.
*G06F 1/16* (2006.01)
(52) U.S. Cl.
USPC .............. 361/679.02; 361/679.3; 361/679.55; 455/90.3; 455/556.1; 455/556.2; 455/575.1
(58) Field of Classification Search ............. 361/679.02; 455/90.3
See application file for complete search history.

(56) References Cited

U.S. PATENT DOCUMENTS

| 6,641,533 | B2 * | 11/2003 | Causey et al. ................. 600/300 |
| 7,071,926 | B2 | 7/2006 | Kusuda et al. |
| 7,539,510 | B2 * | 5/2009 | Toyoda et al. ............. 455/550.1 |
| 7,727,467 | B2 * | 6/2010 | Burke et al. .................. 422/412 |
| 7,947,222 | B2 * | 5/2011 | Bae et al. ........................ 422/50 |
| 7,986,921 | B2 * | 7/2011 | Hedtke et al. ............... 455/90.3 |
| 8,145,267 | B2 * | 3/2012 | Okuda et al. ............... 455/556.1 |
| 2003/0068987 | A1 * | 4/2003 | Dufosse et al. ................ 455/90 |
| 2004/0235446 | A1 * | 11/2004 | Flaherty et al. ............... 455/352 |
| 2006/0229502 | A1 | 10/2006 | Pollock et al. |
| 2008/0015422 | A1 | 1/2008 | Wessel |
| 2008/0146277 | A1 * | 6/2008 | Anglin et al. ............... 455/556.1 |
| 2008/0300572 | A1 | 12/2008 | Rankers et al. |
| 2009/0099509 | A1 * | 4/2009 | Estes et al. ...................... 604/66 |
| 2010/0098583 | A1 * | 4/2010 | Drucker et al. ................. 422/56 |
| 2010/0113896 | A1 | 5/2010 | Cadio et al. |
| 2010/0159982 | A1 * | 6/2010 | Verri Lima ................. 455/556.1 |
| 2010/0198142 | A1 | 8/2010 | Sloan et al. |
| 2011/0111814 | A1 * | 5/2011 | Man et al. .................. 455/575.7 |
| 2011/0151949 | A1 * | 6/2011 | Wen et al. .................. 455/575.7 |

FOREIGN PATENT DOCUMENTS
WO 99/63394 12/1999

OTHER PUBLICATIONS

The World's First Wireless Touchscreen Diabetes Pump. From Cellnovo, a medical device innovator Website. http://www.cellnovo.com/. Accessed Jul. 23, 2010.

* cited by examiner

*Primary Examiner* — Anthony Q Edwards
(74) *Attorney, Agent, or Firm* — Harness, Dickey

(57) ABSTRACT

A handheld diabetes manager having a blood glucose measurement engine comprises a housing having a blood glucose measuring engine and a printed circuit board disposed in the housing. A touch screen can be coupled to the housing. The touch screen can have a transparent portion surrounded by a non-transparent portion. The non-transparent portion can have adhesive thereon that seals the touch screen to the housing. A flexible connector can electrically connect at least two independent electrical leads between the touch screen and the printed circuit board. An antenna assembly can be disposed in the housing and comprise a molded carrier, a conductive portion on the molded carrier and a speaker. The conductive portion can be electrically connected to the printed circuit board and be configured to receive a radio signal. The carrier can include a recess that receives the speaker and is configured to project sound from the speaker.

16 Claims, 11 Drawing Sheets

HANDHELD DIABETES MANAGER WITH TOUCH SCREEN DISPLAY

FIELD

The present disclosure relates to diabetes care medical devices used for diagnostics and therapy and more particularly to a handheld diabetes manager with a blood glucose meter and having a touch screen display.

BACKGROUND

This section provides background information related to the present disclosure which is not necessarily prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such blood glucose, is typically obtained from a capillary blood sample with a lancing device and is then measured with a handheld blood glucose meter. Interstitial glucose levels can be obtained from a continuous glucose sensor worn on the body. Prescribed therapies can include insulin, oral medications, or both. Insulin can be delivered with a syringe, an ambulatory infusion pump, an insulin patch or combinations thereof. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient recorded logs, from laboratory tests, and from healthcare professional recommendations. Medical devices include bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, and blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

Additionally, there is a need to provide such a handheld patient device that can offer touch screen convenience while still meeting regulatory (such as Food and Drug Administration) cleaning requirements. Furthermore, there is a need to provide an internal component configuration that can optimize the internal space of the handheld device.

SUMMARY

This section provides a general summary of the disclosure, and is not a comprehensive disclosure of its full scope or all of its features.

A handheld diabetes manager having a blood glucose measurement engine comprises a housing having a blood glucose measurement engine and a printed circuit board disposed in the housing. A touch screen can be coupled to the housing. The touch screen can have a transparent portion surrounded by a non-transparent portion. The non-transparent portion can have adhesive thereon that seals the touch screen to the housing. A flexible connector can electrically connect at least two independent electrical leads between the touch screen and the printed circuit board. An antenna assembly can be disposed in the housing and comprise a molded carrier, a conductive portion arranged on the molded carrier and a speaker. The conductive portion can be electrically connected to the printed circuit board and be configured to receive a radio signal. The carrier can include a recess that receives the speaker and is configured to project sound from the speaker.

According to additional features, the touch screen can comprise a first electrode film disposed on a substrate. The touch screen can further comprise a second electrode film. The first electrode film can be disposed intermediate the second electrode film and the substrate. The touch screen can further comprise a graphic film disposed on the second electrode film. At least two independent electrical pins can connect the two electrical leads respectively to the touch screen. The flexible connector can have a first segment that connects to the electrical pins, a second segment that connects to the printed circuit board and an intermediate segment that connects between the first and second segments. The first and second segments can extend along parallel and offset planes.

The molded carrier can include two pairs of opposing sidewalls that cooperatively form a recess that receives the speaker. The molded carrier can define an aperture that is configured to receive a fastener that couples the carrier to the housing. The molded carrier can include a support wall that generally connects between the first and second pairs of opposing sidewalls. The support wall can extend along a plane that is transverse to respective planes of each of the opposing sidewalls. The support wall can be located substantially at a midpoint of each of the opposing sidewalls. The recess can define an outlet that is configured to project sound from the speaker. The support wall can be positioned intermediate the speaker and the outlet. A foam member can be disposed intermediate the speaker and the support wall. The foam and the support wall can both define substantially aligned openings.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
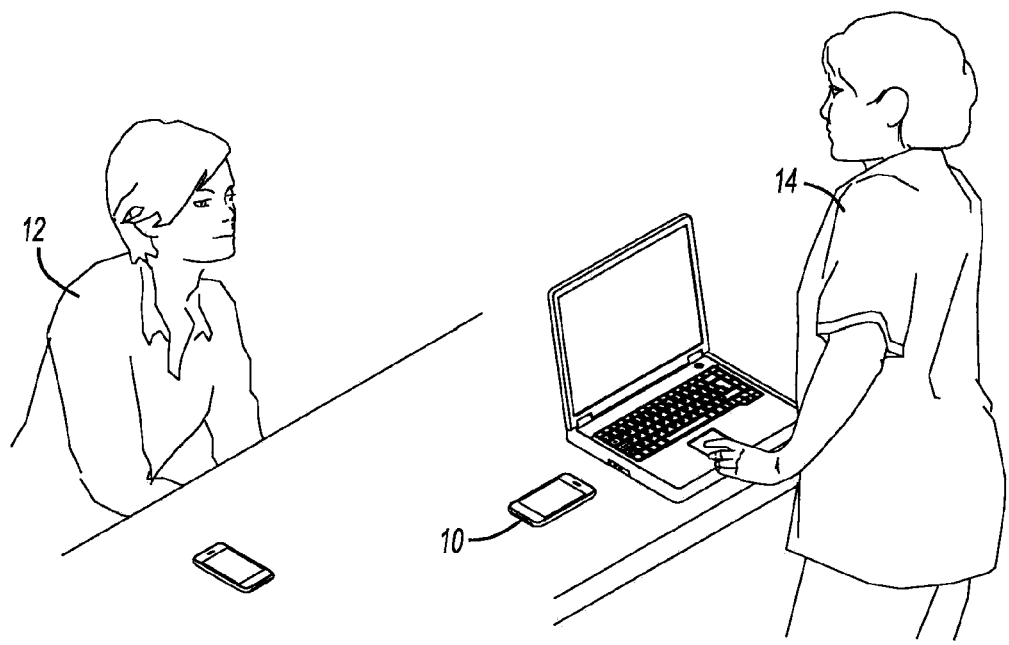
FIG. 1 shows a patient and a treating clinician with a handheld diabetes manager according to the present teachings.
Figure 2:
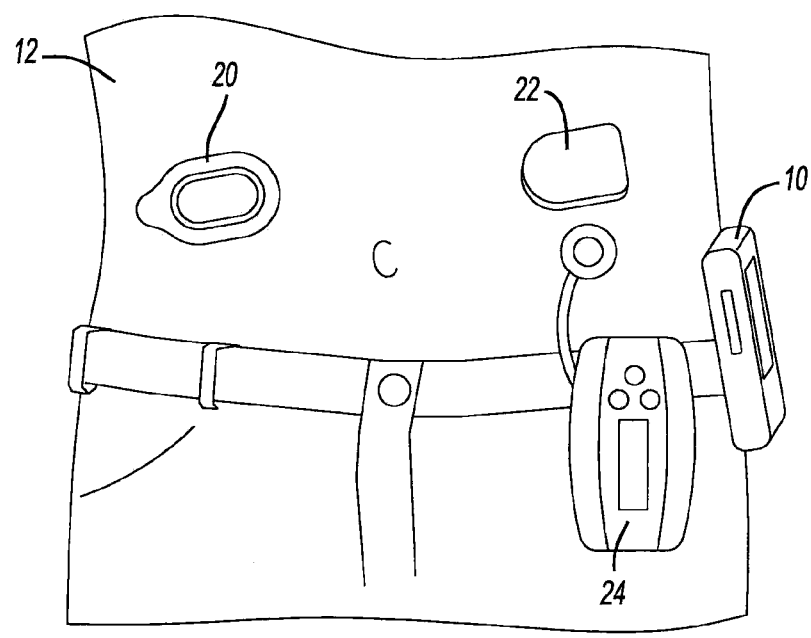
FIG. 2 shows a patient with an exemplary continuous glucose monitor (CGM), first ambulatory insulin infusion pump, second ambulatory insulin infusion pump, and handheld diabetes manager.

With initial reference to FIG. 1, a handheld diabetes manager constructed in accordance to one example of the present teachings is shown and generally identified at reference numeral 10. FIG. 1 also shows a patient 12 with diabetes and a clinician 14 in a clinic environment, the clinician 14 and patient 12 discussing various devices for managing diabetes including the handheld diabetes manager 10. For illustrative purposes, FIG. 2 shows the patient 12 with diabetes with the handheld diabetes manager 10, a continuous glucose monitor (CGM) 20, a first ambulatory insulin infusion pump 22, and a second ambulatory insulin infusion pump 24.

Persons with diabetes include persons with metabolic syndrome, pre-diabetes, type 1 diabetes, type 2 diabetes, gestational diabetes, and other types of diabetes and are collectively referred to as the patient 12 herein. Healthcare providers for diabetes are diverse and include nurses, nurse practitioners, physicians, and endocrinologists and are collectively referred to as the clinician 14 herein. During a healthcare consultation, a patient 12 typically shares with a clinician 14 a variety of patient data including blood glucose measurements, continuous glucose monitor data, insulin infused, food and beverages consumption, exercise, and other lifestyle information. This patient data can be recorded manually on a patient diary or other tools such as an Accu-Chek® 360 View Blood Glucose Analysis System form or electronically on a handheld diabetes manager, such as the handheld diabetes manager 10, or electronically on personal computer using diabetes analysis software, or electronically on a web-based diabetes analysis site, or a combination of these means. The clinician 14 will often obtain additional patient biomarker data such as measurements of HbA1C, cholesterol levels, triglycerides, blood pressure, and weight. The clinician 14 can analyze the patient data using manual techniques, electronically using diabetes analysis software, or a web-based diabetes analysis site, or a combination of these means. After analyzing the patient data along with the patient's adherence to the previously prescribed therapy, the clinician 14 can decide whether to modify the therapy for the patient 12. In considering whether to modify the therapy, the clinician 14 may need to balance the interests of the patient 12, the payer (not shown), and the clinician 14.

Figure 3:
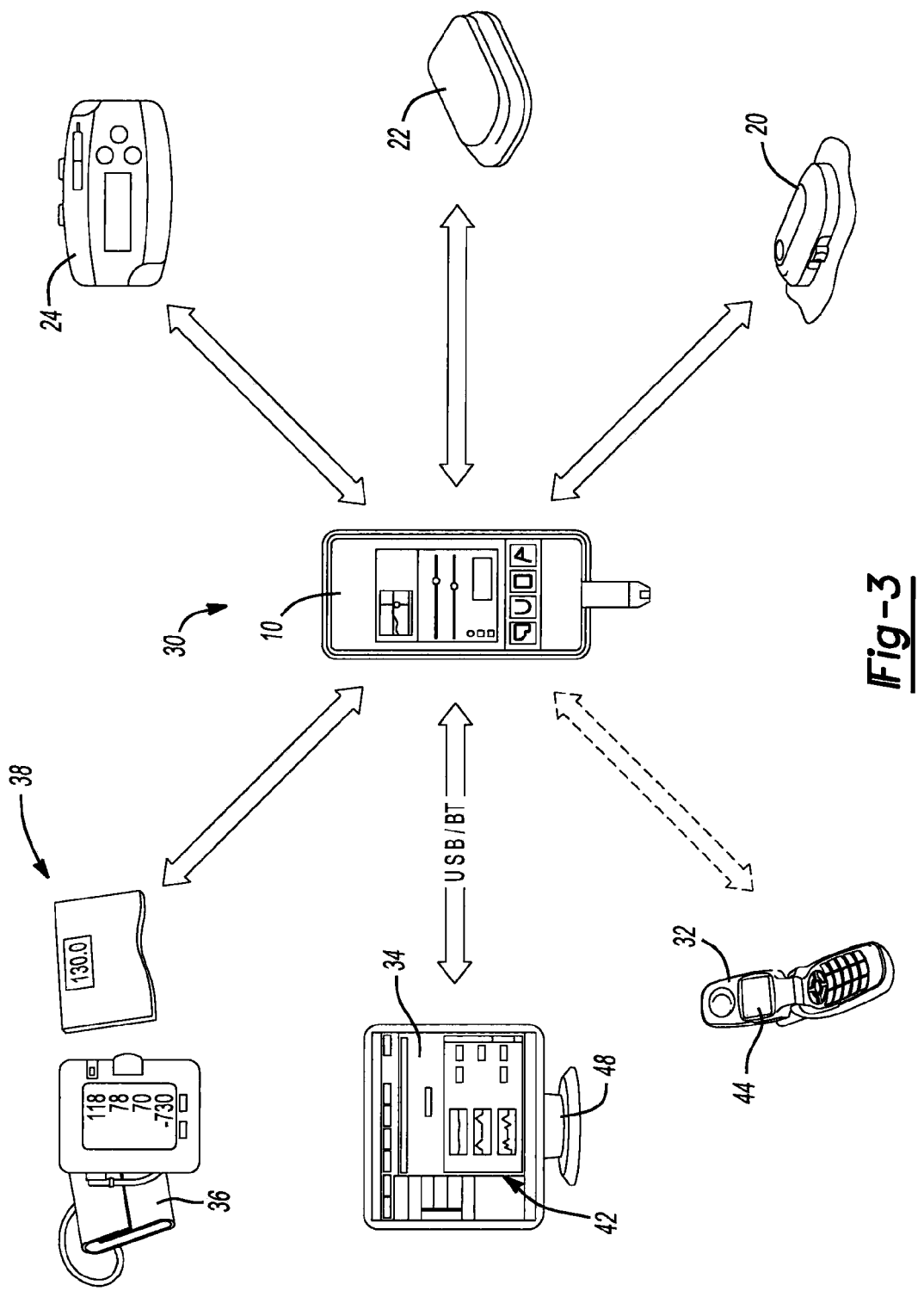
FIG. 3 shows an exemplary diabetes care system of devices used by patients and clinicians to manage diabetes.
Figure 4:
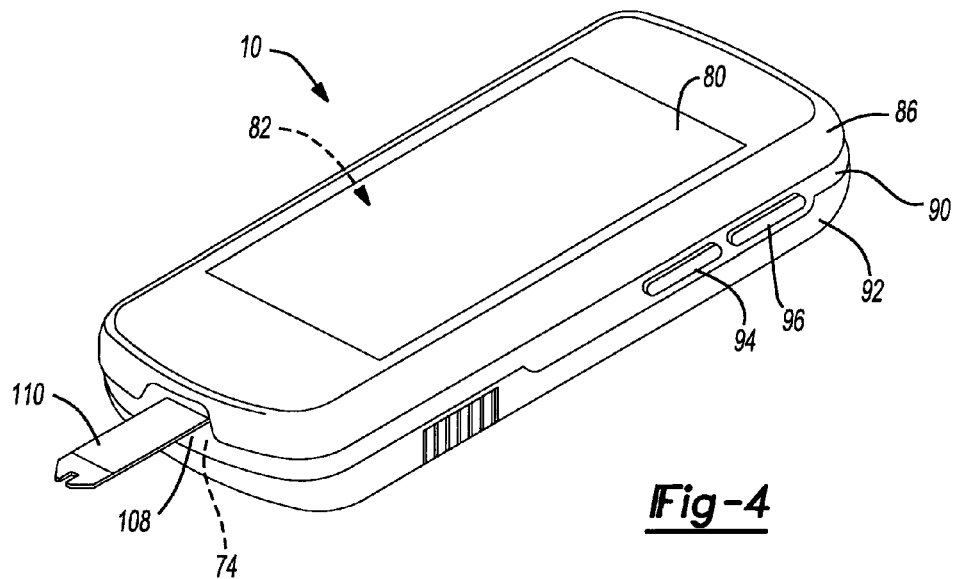
FIGS. 4-8 show various isometric views of the handheld diabetes manager of FIG. 1.
Figure 5:
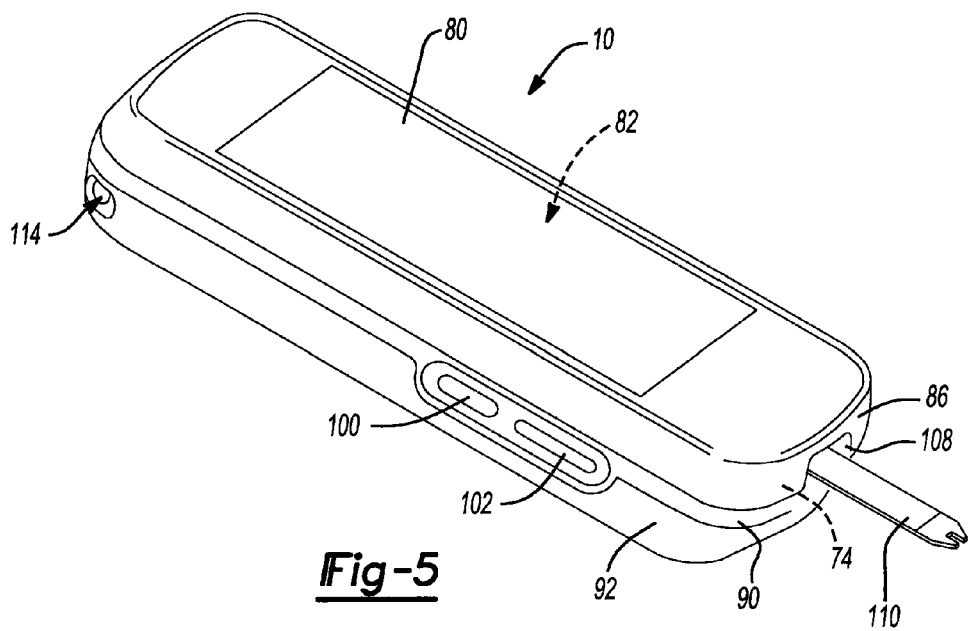
Figure 6:
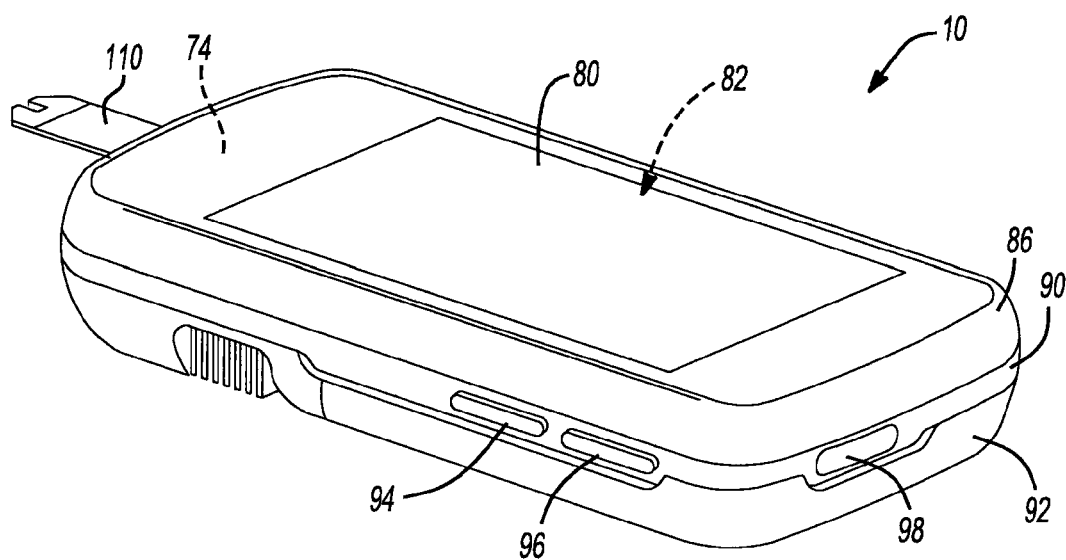
Figure 7:
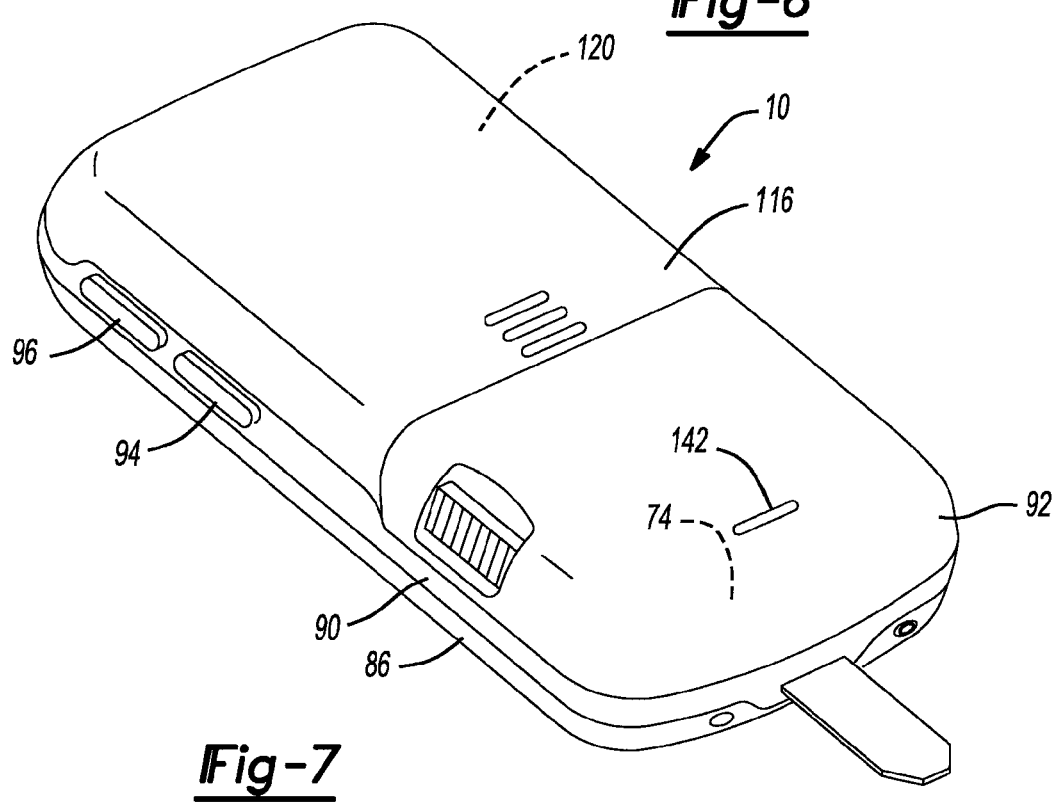
Figure 8:
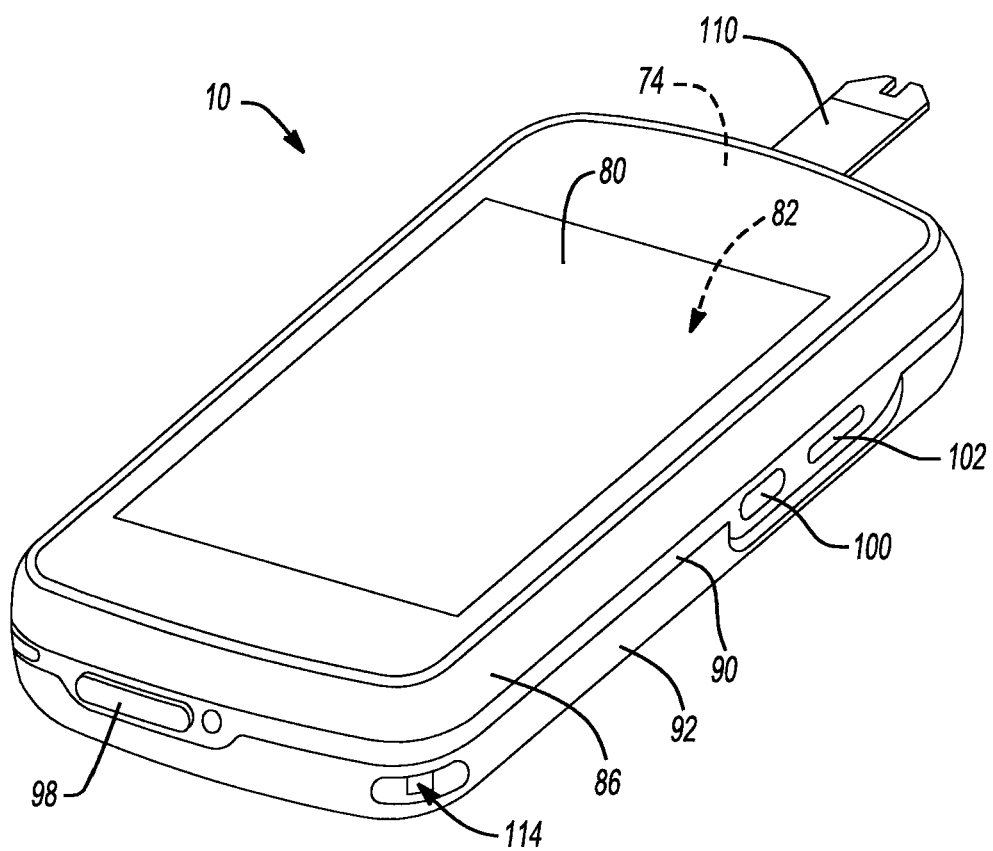

FIG. 3 shows a diabetes care system of devices 30 used by clinicians and patients with diabetes to manage diabetes according to the present teachings. The system of devices 30 can include one or more of the following devices: the handheld diabetes manager 10, the first ambulatory insulin infusion pump 22, the second ambulatory insulin infusion pump 24, the continuous glucose monitor (CGM) 20, the mobile phone 32, diabetes analysis software and pump configuration software 34, a health (such as blood pressure) monitor 36 and various health care devices 38. The handheld diabetes manager 10 is configured as the system hub in this embodiment. However, other devices such as the first ambulatory insulin infusion pump 22 or the mobile phone 32 can serve as the system hub according to other embodiments. Communications among the system of devices 30 can be performed using, for example, a wireless protocol such as Bluetooth or a proprietary protocol that operates IEEE 11073 as extended using guidelines provided by the Continual® Health Alliance Design Guidelines. Healthcare records systems such as Microsoft® HealthVault™ and Google™ Health can be used by the patient 12 and clinician 14 to exchange information. The CGM 20 uses a subcutaneous sensor to sense and monitor the amount of glucose in the blood of the patient 12 and communicates corresponding readings to the handheld diabetes manager 10.

The handheld diabetes manager 10 performs various tasks including measuring and recording blood glucose levels, determining an amount of insulin to be administered to the patient 12 via the insulin infusion pump 22 or 24, receiving patient data via a user interface, archiving the patient data, etc. The handheld diabetes manager 10 periodically receives readings from the CGM 20 indicating insulin level in the blood of the patient 12. The handheld diabetes manager 10 transmits instructions to the insulin infusion pump 22 or 24, which delivers insulin to the patient 12. Insulin can be delivered in a scheduled manner in the form of a basal dose, to maintain a predetermined insulin level in the blood of the patient 12. Additionally, insulin can be delivered in the form of a bolus dose, which raises the amount of insulin in the blood of the patient 12 by a predetermined amount.

The CGM patch 20 is a user-wearable continuous glucose monitoring patch. The CGM patch 20 collects CGM data and wirelessly transmits the CGM data to the handheld diabetes manager 10.

The mobile messenger 44 can be a mobile phone, pager, or other communications system. The mobile messenger 44 comprises a messenger subsystem that formats messages selected for transmission to an external communications network (not shown). The mobile messenger 44 accepts message requests from the handheld diabetes manager 10.

The health care devices 38 can include the health monitor 36, weight scale, pedometer, fingertip pulse oximeter, thermometer, or other device that obtains personal health information and is capable of communicating the health information to the handheld diabetes manager 10 through a data output channel such as a wireless or USB transport using a communications protocol such as ISO/IEEE 11073 extended using guidelines from Continual® Health Alliance.

The first insulin infusion pump 22 can have an insulin reservoir and can be configured to deliver insulin to the patient 12. The first insulin infusion pump 22 can also communicate data to the handheld diabetes manager 10. The data can include amounts of insulin delivered to the patient 12, corresponding times of delivery, and pump status. The handheld diabetes manager 10 and the first insulin infusion pump 22 can communicate using a wireless communication protocol such as Bluetooth. Other wireless or wireline communication protocols can also be used. It will be appreciated that the second insulin infusion pump 24 can be configured similarly.

The handheld diabetes manager 10 includes a blood glucose measurement engine 74. The blood glucose measurement engine 74 can determine a blood glucose value derived from a blood sample placed on a test strip as will be described herein.

With general reference now to FIGS. 4-8, additional features of the handheld diabetes manager 10 will be described. The handheld diabetes manager 10 is designed to have an appearance similar to a consumer electronics device and a popular Windows CE operating system, so persons with diabetes can manage their diabetes more discretely using a more familiar user interface. The handheld diabetes manager 10 can have a touch screen 80 that supports gesturing. The touch screen 80 overlays a thin film transistor (TFT) display 82. The TFT display 82 can display multiple colors for graphic displays for an improved user interface and the presentation of video. In one example, the TFT display 82 can be a liquid crystal diode (TFT-CD) display. The touch screen 80 can be a resistive touch screen. A top housing 86 can generally support the touch screen 80 at a position intermediate the touch screen 80 and the TFT display 82.

A center frame 90 can be positioned generally between the top housing 86 and a bottom housing 92. The center frame 90 can generally support buttons 94 and 96 on one side (FIG. 4) and provide access to a USB port 100 and SD port 102 on an opposite side. The buttons 94 and 96 can be indexing buttons. The center frame 90 can also define an access port 108 for insertion of a test strip 110 to perform blood glucose measurements using the blood glucose measurement engine 74. The bottom housing 92 can further comprise a lanyard 114.

The lanyard 114 can be used to support a flexible member, such as a string or lace for attaching to the handheld diabetes manager 10. A battery cover 116 can be slidably coupled to the bottom housing 92 to securely retain a battery 118 relative to the bottom housing 92. The battery 118 can be a user-replaceable single lithium-ion battery with integrated safety circuit.

Figure 9:
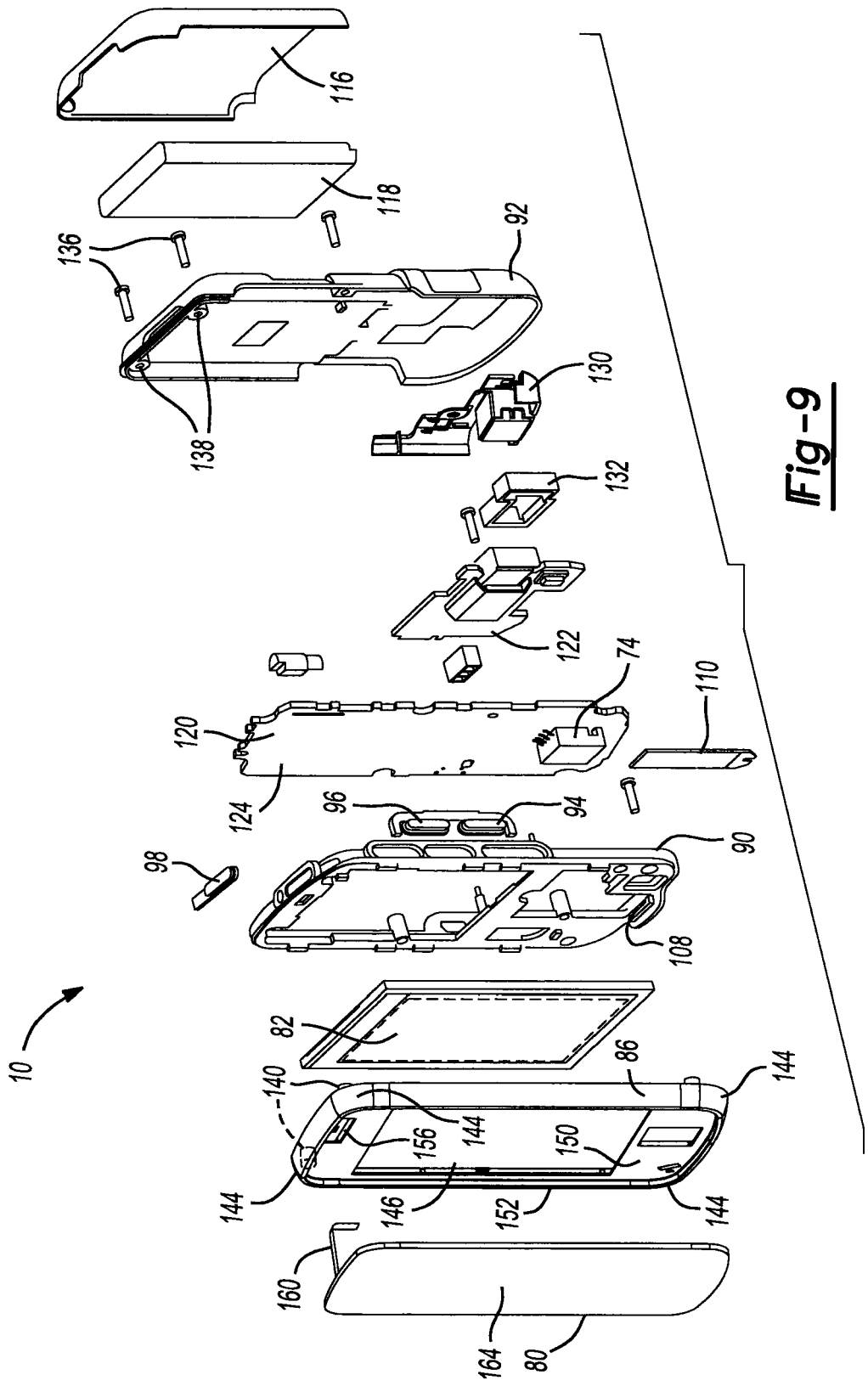
FIG. 9 shows an exploded view of an exemplary handheld diabetes manager according to the present teachings.

With specific reference now to FIG. 9, additional components of the handheld diabetes manager 10 will be described in greater detail. A printed circuit board (PCB) 120 can be positioned generally intermediate the center frame 90 and the bottom housing 92. A communications circuit 122 can be generally electrically connected to the PCB 120. The PCB 120 can incorporate a processor 124 that has integrated power management and system interfaces with internal nonvolatile memory. One suitable processor is a 32-bit ARM926SJ-E core processor. External memory can be flash memory for program and data storage and can be communicated such as through the SD port 102.

An antenna assembly 130 can be arranged generally between the communications circuit 122 and the bottom housing 92. A support member 132 can provide structural support for the antenna assembly 130 relative to the communications circuit 122. A series of fasteners 136 can be located through passages 138 defined through the bottom housing 92 and be threadably connected to complementary bosses 140 extending from the top housing 86. A speaker passage 142 (FIG. 7) can be provided through the bottom housing 92.

The blood glucose measurement engine 74 can be arranged against the PCB 120. The blood glucose measurement engine 74 can be of the type included in the Accu-Chek® Aviva Blood Glucose Meter, portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. The test strips 110, also known as disposable biosensors, are used with an integrated collection device to receive a sample of capillary blood which is exposed to an enzymatic reaction and measured by electrochemistry techniques, optical techniques, or both to measure blood glucose. An example of a test strip 110 and blood glucose measurement engine 74 is disclosed in U.S. Pat. No. 7,727,467 "Reagent stripe for test strip", assigned to Roche Diagnostic Operations, Inc., which is hereby incorporated by reference. The blood glucose measurement engine 74 provides a means to determine a blood glucose value derived from a blood sample placed on a test strip 110 and to send that data for viewing on the TFT display 82.

Figure 10:
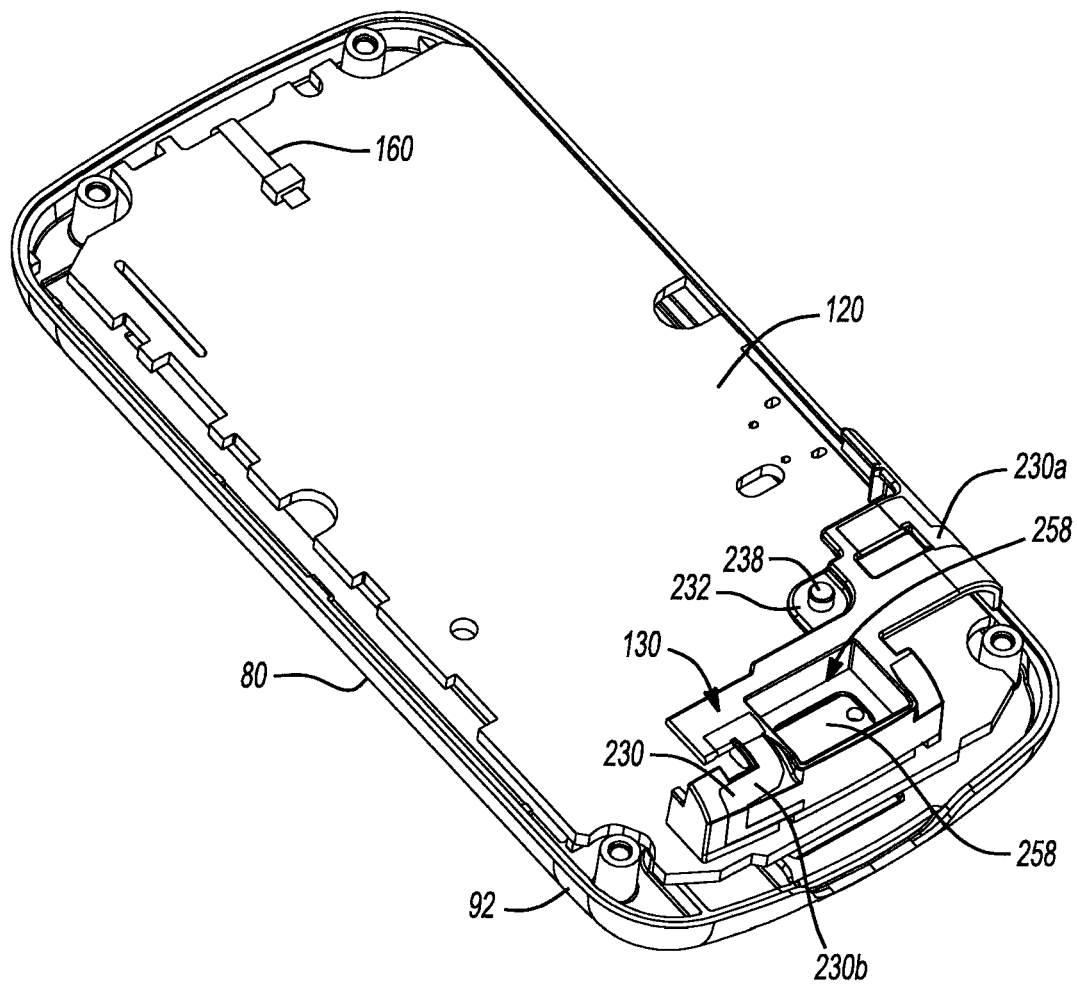
FIG. 10 is a rear perspective view of the handheld diabetes manager of FIG. 9 shown with the bottom housing, battery and battery cover removed.

With continued reference to FIG. 9 and additional reference now to FIGS. 10 and 11, the top housing 86 will be described in greater detail. The top housing 86 can generally have a rectangular profile that includes rounded corners 144. An opening 146 can be formed through the top housing 86 that generally provides a viewing area to observe the TFT display 82. A support surface 150 can be recessed a distance relative to a front edge 152. The support surface 150 can receive the touch screen 80 in a fluid-tight, sealed relationship as will be described herein. A passage 156 can be formed through the top housing 86 for receipt of a flexible connector 160 that is electrically connected between the touch screen 80 and the PCB 120.

Figure 11:
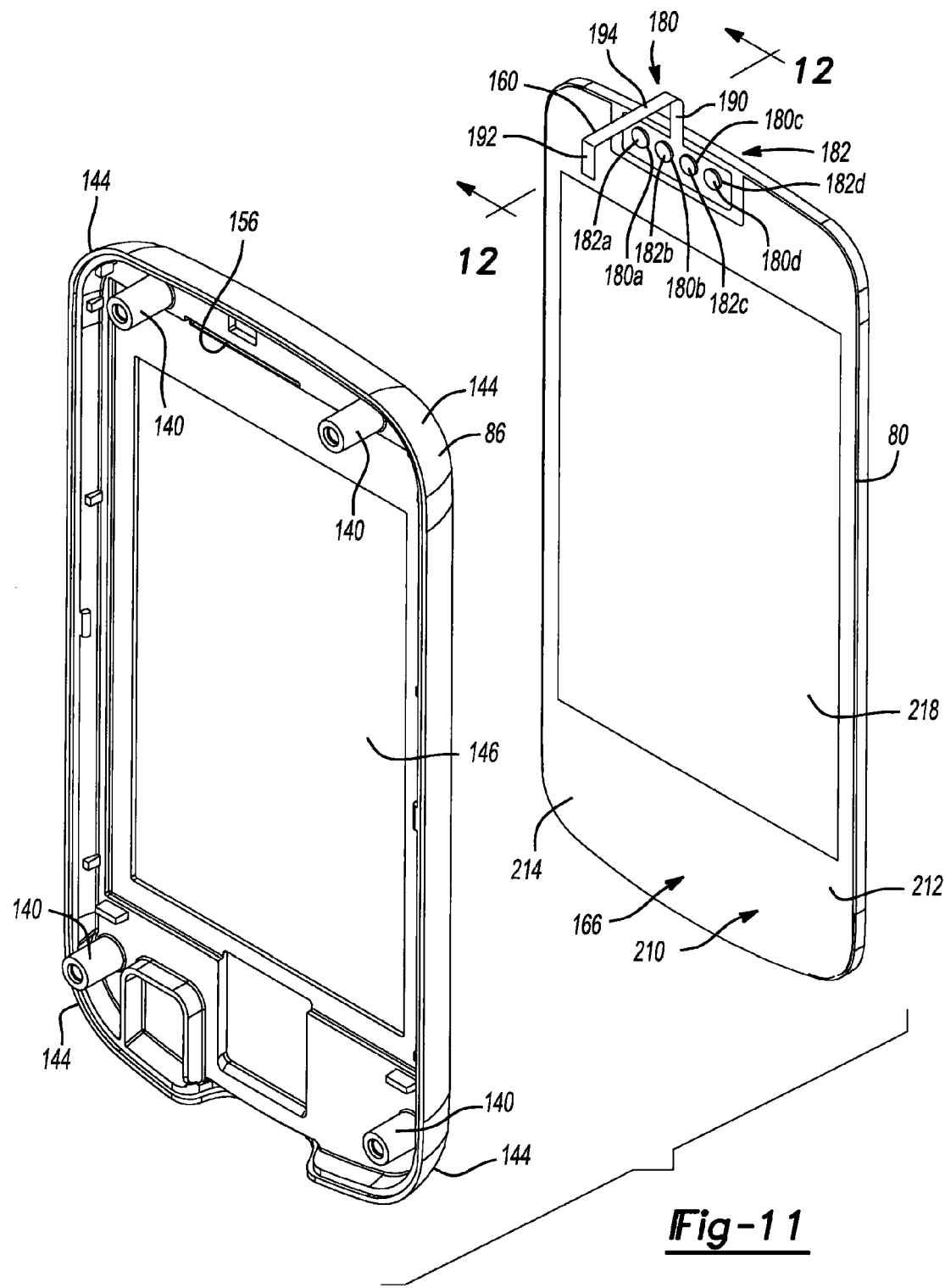
FIG. 11 is a rear exploded view of the touch window and top housing of FIG. 9.

The touch screen 80 generally includes a front touch surface 164 (FIG. 9) and a rear connection surface 166 (FIG. 11). The rear connection surface 166 can be securely connected to the support surface 150 of the top housing 86 by way of adhesive as will be described in greater detail.

Figures 12, 13:
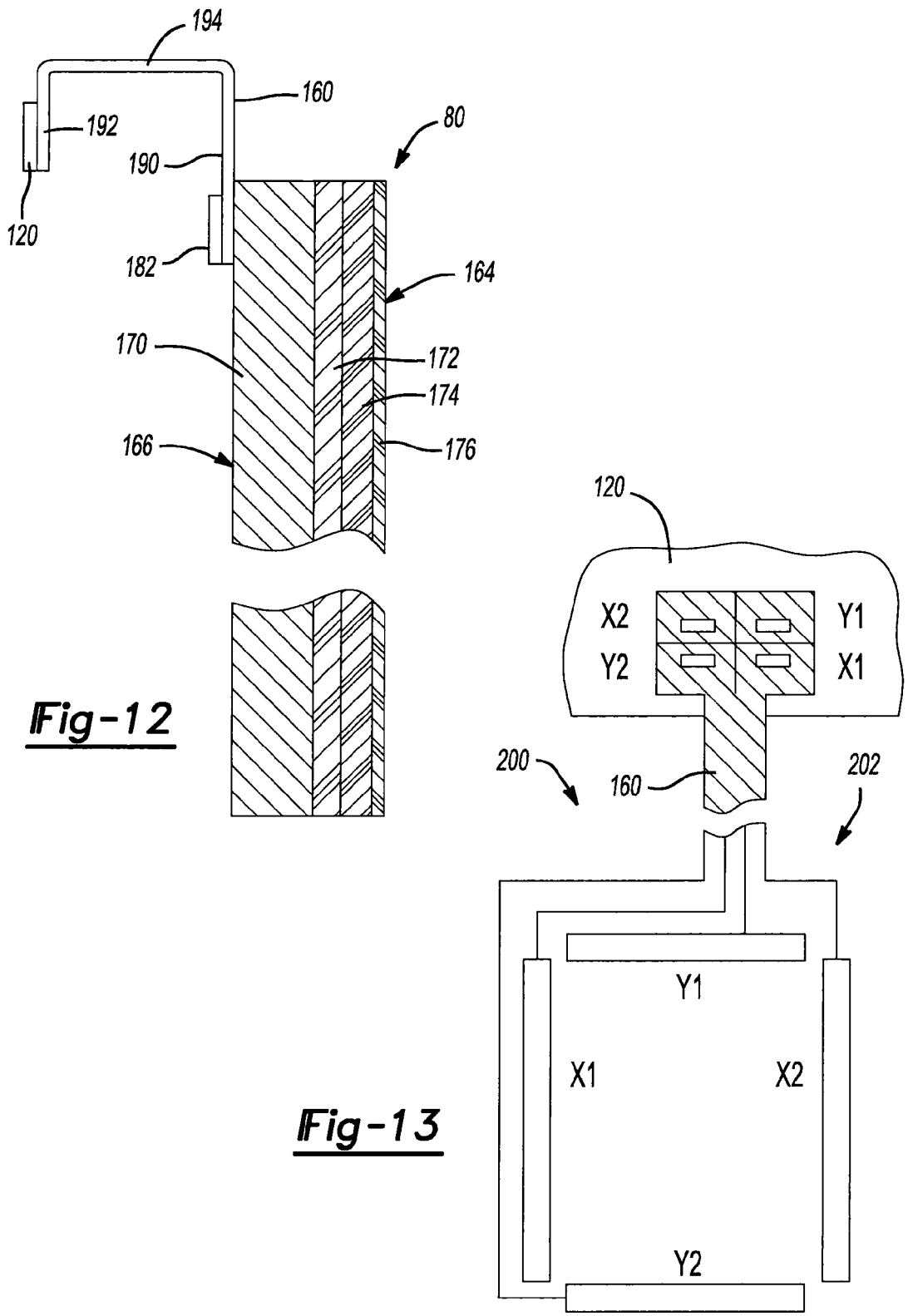
FIG. 12 is a cross-sectional view of the touch window taken along line 12-12 of FIG. 11.
FIG. 13 shows an electrical schematic for a touch window sensor of the touch window of FIG. 11.

With reference now to FIGS. 11 and 12, the touch screen 80 can generally include a substrate 170 that provides the rear connection surface 166, a first (lower) electrode film 172 disposed on the substrate 170, a second (upper) electrode film 174 disposed on the lower electrode film 172 and a graphic film 176 disposed on the upper electrode film 174. The upper electrode film 174 provides the front touch surface 164. In this regard, the touch screen 80 comprises a first electrode film 172 disposed on the substrate 170. The touch screen 80 further comprises a second electrode film, the first electrode film 172 disposed intermediate the second electrode film 174 and the substrate 170. The graphic film 176 can be disposed on the second electrode film 174. One suitable touch screen is manufactured by Nissha Printing Co., Ltd of Tokyo, Japan.

Referring again to FIG. 11, in the exemplary configuration, the flexible connector 160 can provide four distinct electrical leads collectively referred to at reference numeral 180 and individually identified at reference numerals 180a, 180b, 180c and 180d, respectively. Each of the electrical leads 180 can connect to the touch screen 80 by way of pins collectively referred to at reference numeral 182 and individually identified at reference numerals 182a, 182b, 182c and 182d, respectively. The flexible connector 160 can have a first segment 190 that connects to the electrical pins 182, a second segment 192 that connects to the PCB 120 and an intermediate segment 194 that connects between the first and the second segments 190 and 192, respectively. The flexible connector 160 flexes to achieve an orientation, such that the first and second segments 190 and 192 occupy planes that are generally parallel and offset relative to each other. The intermediate segment 194 can occupy a plane that is generally transverse to the planes occupied by the first and second segments 190 and 192. In general, the intermediate segment 194 can pass through the passage 156 in the top housing 86, such that the second segment 192 can electrically connect with the PCB 120.

FIG. 13 illustrates an exemplary electrical schematic 200 of a touch window sensor 202 that can be integrated into the touch screen 80. As is known in the art, the touch window sensor 202 can be configured to sense the touch of a user's finger on the front touch surface 164 of the touch screen 80. In this regard, circuitry on the PCB 120 can correlate a position that a user has touched the touch screen 80 with a location of an item presented on the TFT display 82.

Referring to FIG. 11, in one configuration, adhesive 210 is applied across a boundary 212 of the rear connection surface 166. The adhesive 210 can be pressure sensitive acrylic adhesive. The adhesive 210 can therefore be applied around the boundary 212 to create a generally non-transparent portion 214 that surrounds a transparent portion 218. As used herein, the term "non-transparent" is used to denote a portion of the touch screen 80 that has adhesive applied thereon. It will be appreciated that in some instances that the non-transparent portion 214 can be at least partially transparent.

The transparent portion 218 can have a generally transparent viewing area that corresponds to the opening 146 in the top housing 86 for viewing the TFT display 82. By applying adhesive 210 around the entire boundary 212, a liquid-tight seal can be made between the boundary 212 of the rear connection surface 166 on the touch screen 80 and the support surface 150 of the top housing 86. A liquid-tight seal can then be realized between the touch screen 80 and the top housing 86. In some examples, the liquid-tight seal can provide a hermetic seal. Since the touch screen 80 is the face of the handheld diabetes manager 10, the touch screen 80 is required to meet specific regulatory (such as Food and Drug Administration) guidelines that pertain to cleanliness. In this regard, the touch screen 80 must be designed, such that debris is not easily retained by the touch screen 80 and such that touch screen 80 can be cleaned with a liquid and cloth without liquid intrusion between the touch screen 80 and the top housing 86 of the handheld diabetes manager 10. The configuration of the touch screen 80, adhesive 210 and top housing 86 of the present disclosure meets these guidelines.

Figure 14:
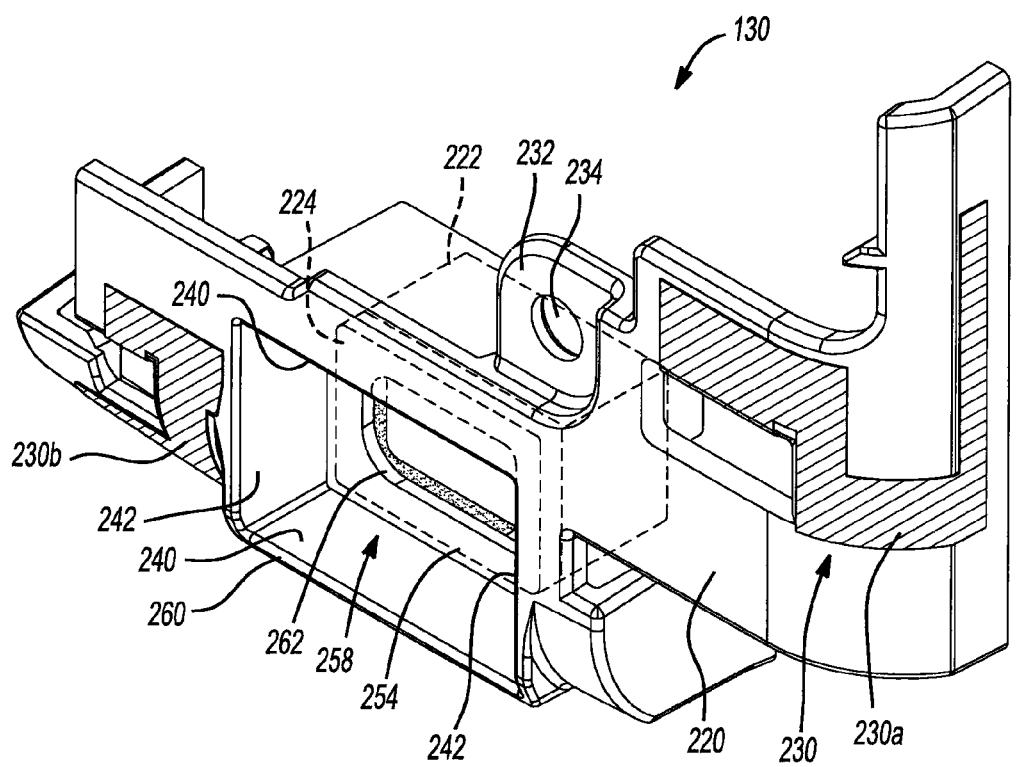
FIG. 14 is a front perspective view of an antenna assembly of the handheld diabetes manager.
Figure 15:
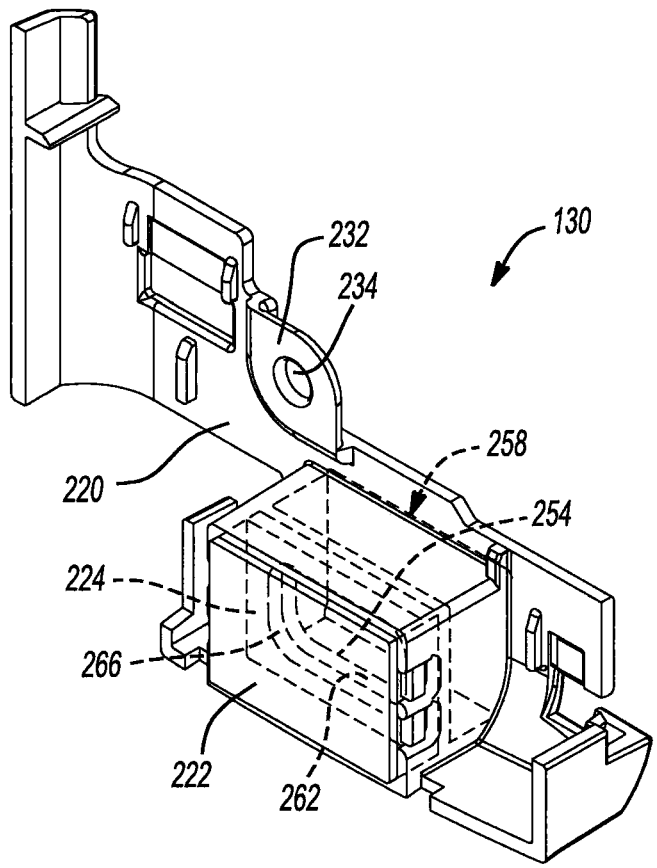
FIG. 15 is a rear perspective view of the antenna assembly of FIG. 14.
Figure 16:
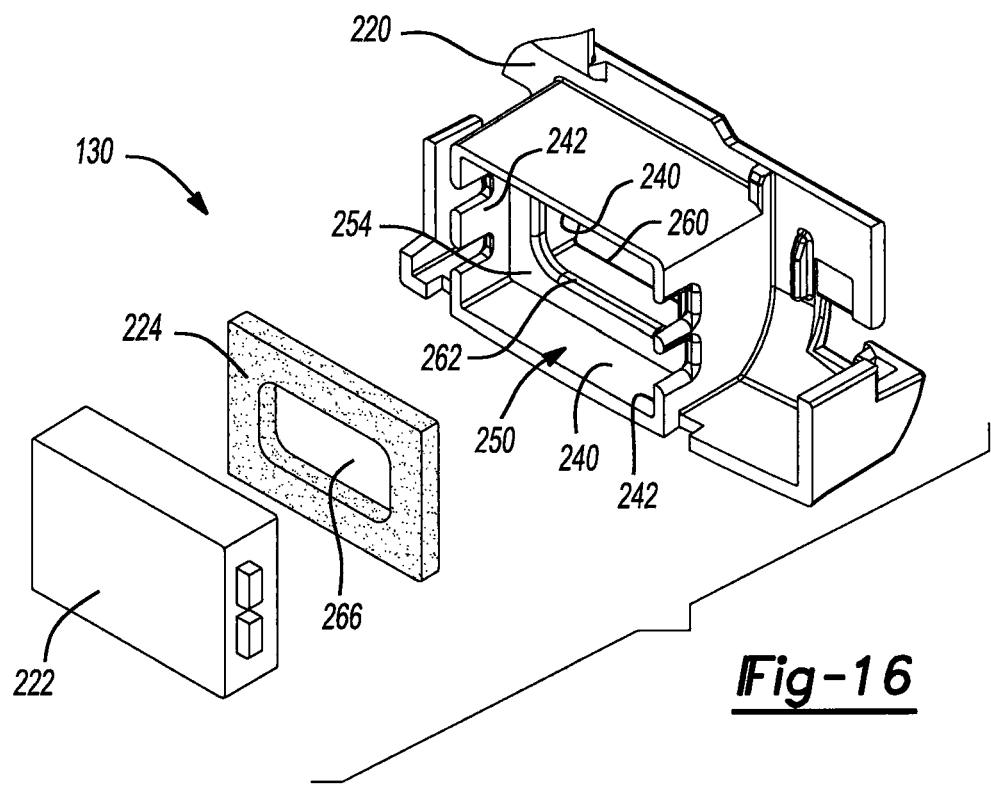
FIG. 16 is an exploded rear perspective view of the antenna assembly of FIG. 15.

With reference now to FIGS. 14-16, the antenna assembly 130 will be described in further detail. The antenna assembly 130 can generally include a molded carrier 220, a speaker 222 and a piece of foam 224. A conductive portion 230 can be arranged and supported on the molded carrier 220. In the example shown, two conductive portions 230a and 230b collectively comprise the conductive portion 230. A single conductive portion or multiple separate conductive portions can be incorporated as desired. According to one example, the conductive portion 230 can be manufactured by a laser direct structuring. In this regard, the molded carrier 220 can be processed using a laser to remove the base plastic resin in desired areas to expose and sinter copper particles in the resin. The exposed copper is then plated with more copper, nickel, and finally gold to form the conductive portion 230 in the desired shape.

The conductive portion 230 can be configured to receive a radio signal, such as any of the wireless signals discussed herein, and be electrically connected to the PCB 120. The molded carrier 220 can include a mounting tab 232 that defines an aperture 234. The aperture 234 can receive a fastener 238 (FIG. 10) that securely connects the molded carrier 220 to the center frame 90. The molded carrier 220 can generally comprise a first and a second pair of opposing sidewalls 240 and 242, respectively. In one example, the first pair of opposing sidewalls 240 can be parallel relative to each other and the second pair of opposing sidewalls 242 can be parallel relative to each other. In one example, the first and second pairs of opposing sidewalls 240 and 242 can cooperate to form a recess 250 that receives and supports the speaker 222 and the foam 224.

A support wall 254 can extend generally transversely between the respective first and second pairs of opposing sidewalls 240 and 242. In one example, the support wall 254 extends along a plane that is transverse to respective planes of each wall of the first and second pairs of opposing sidewalls 240 and 242. The foam 224 can be generally positioned against the support wall 254 to provide vibration damping between the speaker 222 and the molded carrier 220. A chute or chimney 258 can be formed by the recess 250 between an outlet 260 and the support wall 254. The chimney 258, and the recess 250 as a whole, can facilitate sound transmission from the speaker 222 to project sound emitted from the speaker 222. An opening 262 can be formed through the support wall 254 to pass sound emitted from the speaker 222 through the foam 224 and through the support wall 254. In one example, the foam 224 can also provide an opening 266 that coincides with the opening 262 in the support wall 254. The antenna assembly 130 of the present disclosure can provide an efficient packaging arrangement where valuable space within the handheld diabetes manager 10 can be used for both components of an antenna (the conductive portion 230) as well as providing support for the speaker 222.

What is claimed is:

1. A handheld diabetes manager having a blood glucose measurement engine, the handheld diabetes manager comprising:
   a housing;
   a blood glucose measuring engine disposed in the housing;
   a printed circuit board disposed in the housing;

a touch screen coupled to the housing, the touch screen having a transparent portion surrounded by a non-transparent portion, the non-transparent portion having adhesive thereon that seals the touch screen to the housing;

a flexible connector that electrically connects at least two independent electrical leads between the touch screen and the printed circuit board; and an antenna assembly disposed in the housing and comprising a molded carrier, a conductive portion arranged on the molded carrier, and a speaker, wherein the conductive portion is electrically connected to the printed circuit board and is configured to receive a radio signal and wherein the carrier includes two pairs of opposing sidewalls that form a recess that receives the speaker and is configured to project sound from the speaker.

2. The handheld diabetes manager of claim 1 wherein the touch screen comprises a first electrode film disposed on a substrate.

3. The handheld diabetes manager of claim 2 wherein the touch screen further comprises a second electrode film, the first electrode film disposed intermediate the second electrode film and the substrate.

4. The handheld diabetes manager of claim 3 wherein the touch screen further comprises a graphic film disposed on the second electrode film.

5. The handheld diabetes manager of claim 2, further comprising at least two independent electrical pins that connect the at least two electrical leads respectively to the touch screen.

6. The handheld diabetes manager of claim 5 wherein the flexible connector has a first segment that connects to the electrical pins, a second segment that connects to the printed circuit board and an intermediate segment that connects between the first and second segments, wherein the first and second segments extend along parallel and offset planes.

7. The handheld diabetes manager of claim 1 wherein the molded carrier defines an aperture configured to receive a fastener that couples the carrier to the housing.

8. The handheld diabetes manager of claim 1 wherein the molded carrier includes a support wall that generally connects between the first and second pairs of opposing sidewalls.

9. The handheld diabetes manager of claim 8 wherein the support wall extends along a plane that is transverse to respective planes of each of the opposing sidewalls and wherein the support wall is located substantially at a midpoint of each of the opposing sidewalls.

10. The handheld diabetes manager of claim 8 wherein the recess defines an outlet that is configured to project sound from the speaker and the support wall is positioned intermediate the speaker and the outlet.

11. The handheld diabetes manager of claim 10, further comprising a foam member disposed intermediate the speaker and the support wall, wherein the foam and the support wall both define substantially aligned openings.

12. A handheld diabetes manager having a blood glucose measurement engine, the handheld diabetes manager comprising:

a housing having a passage;

a blood glucose measuring engine disposed in the housing;

a printed circuit board disposed in the housing;

a touch screen coupled to the housing, the touch screen having a transparent portion surrounded by a non-transparent portion, the non-transparent portion having adhesive thereon that couples the touch screen to the housing and seals the touch screen to the housing; and a flexible connector that electrically connects at least two independent electrical leads between at least two corresponding independent electrical pins on the touch screen and the printed circuit board, wherein the flexible connector has a first segment that connects to the electrical pins, a second segment that connects to the printed circuit board and an intermediate segment that passes through the passage in the housing and connects between the first and second segments, wherein the first and second segments extend along parallel and offset planes.

13. The handheld diabetes manager of claim 12 wherein the touch screen comprises a first electrode film disposed on a substrate, and a second electrode film, the first electrode film disposed intermediate the second electrode film and the substrate and a graphic film disposed on the second electrode film.

14. A handheld diabetes manager having a blood glucose measurement engine, the handheld diabetes manager comprising:

a housing;

a blood glucose measuring engine disposed in the housing;

a printed circuit board disposed in the housing; and an antenna assembly disposed in the housing and comprising a molded carrier, a conductive portion arranged on the molded carrier, and a speaker, wherein the conductive portion is electrically connected to the printed circuit board and is configured to receive a radio signal and wherein the carrier includes two pairs of opposing sidewalls that form a recess that receives the speaker and is configured to project sound from the speaker.

15. The handheld diabetes manager of claim 14 wherein the molded carrier includes a support wall that generally connects between the first and second pairs of opposing sidewalls and wherein the support wall extends along a plane that is transverse to respective planes of each of the opposing sidewalls and wherein the support wall is located substantially at a midpoint of each of the opposing sidewalls.

16. The handheld diabetes manager of claim 15 wherein the recess defines an outlet that is configured to project sound from the speaker and the support wall is positioned intermediate the speaker and the outlet and further comprising a foam member disposed intermediate the speaker and the support wall, wherein the foam and the support wall both define substantially aligned openings.

* * * * *